US007718415B1

(12) United States Patent
Nsereko et al.

(10) Patent No.: US 7,718,415 B1
(45) Date of Patent: May 18, 2010

(54) ACETYL ESTERASE PRODUCING STRAINS AND METHODS OF USING SAME

(75) Inventors: Victor Nsereko, Johnston, IA (US); Christine Dengler, Ankeny, IA (US); Brenda Smiley, Granger, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 28 days.

(21) Appl. No.: 12/035,474

(22) Filed: Feb. 22, 2008

Related U.S. Application Data

(62) Division of application No. 10/947,865, filed on Sep. 23, 2004.

(60) Provisional application No. 60/505,521, filed on Sep. 23, 2003.

(51) Int. Cl.
C12N 1/20 (2006.01)
A23K 1/00 (2006.01)
A23K 3/00 (2006.01)

(52) U.S. Cl. ............ 435/252.5; 426/53; 426/623; 435/252.4; 435/822; 435/839

(58) Field of Classification Search ............ None
See application file for complete search history.

(56) References Cited

U.S. PATENT DOCUMENTS

| | | | |
|---|---|---|---|
| 5,720,971 A | | 2/1998 | Beauchemin et al. |
| 5,840,868 A | * | 11/1998 | Warren et al. ............ 536/23.1 |
| 5,948,454 A | | 9/1999 | Virkki et al. |

FOREIGN PATENT DOCUMENTS

| | | |
|---|---|---|
| WO | WO 93/20714 | 10/1993 |
| WO | WO 01/49129 | 7/2001 |
| WO | WO 02/068666 | 9/2002 |

OTHER PUBLICATIONS

Higerd et al, "Isolation of Two Acetyl Esterases from Extracts of *Bacillus subtilis*", J. of Bacterilogy, Jun. 1973 p. 1184-1192.*
Katz, et al., The Peptide Antibiotics of *Bacillus*: Chemistry, Biogenesis, and Possible Functions, *Bacteriol. Rev.* (1977), 41(2): 449-474.
Gorosito, et al., Effect of Carbon-4 and Carbon-5 Volatile Fatty Acids on Digestion of Plant Cell Wall in Vitro, *J Dairy Sci* (1985), 68: 840-847.
Newbold, et al., The effects of yeast culture on yeast numbers and fermentation in the rumen of sheep, *Proc. Nutr. Soc.*, (1989), 49:47A.
Offer, N.W., Maximising Fibre Digestion in the Rumen: The Role of Yeast Culture, *Biotechnology in the Feed Industry, ed., Alltech Technical Publications*, (1990), pp. 79-96.
Chademana, et al., The Effect of Dietary Inclusion of Yeast Culture on Digestion in the Sheep, *Anim. Prod.* (1990), 50: 483-489.
Nisbet, et al., Effect of a *Saccharomyces cerevisiae* Culture on Lactate Utilization by the Ruminal Bacterium *Selenomonas ruminantium*, *J. Anim. Sci.*, (1991), 69: 4628-4633.
McDonald, et al., *The Biochemistry of Silage*, 2nd ed. Marlow, UK (1991) pp. 130-131.

Martin, et al., Effect of Direct-Fed Microbials on Rumen Microbial Fermentation, *J Dairy Sci*, (1992) 75: 1736-1744.
Erasmus, et al., Effect of Yeast Culture Supplement on Production, Rumen Fermentation, and Duodenal Nitrogen Flow in Dairy Cows, *J Dairy Sci*, (1992) 75: 3056-3065.
Wallace, et al. , Probiotics for Ruminants, *Probiotics: The Scientific Basis*, ed. R. Fuller, (1992), pp. 317-353.
Mutsvangwa, et al., The effect of dietary inclusion of yeast culture (Yea-Sacc) on patterns of rumen fermentation, food intake and growth of intensively fed bulls, *Anim. Prod.*, (1992) 55: 35-40.
Plata, et al., Effect of a yeast culture (*Saccharomyces cerevisiae*) on neutral detergent fiber digestion in steers fed oat straw based diets, *Anim. Feed Sci. Technol*, (1994) 49: 203-210.
Kumar, et al., Effect of *Saccharomyces cerevisiae* yeast culture supplement on ruminal metabolism in buffalo calves given a high concentrate diet, *Anim. Prod.* (1994), 59: 209-215.
Newbold, et al., Mode of action of the yeast *Saccharomyces cerevisiae* as a feed additive for ruminants, *Br J Nutr*, (1996), 76: 249-261.
Callaway, et al., Effects of a *Saccharomyces cerevisiae* Culture on Ruminal Bacteria that Utilize Lactate and Digest Cellulose, *J Dairy Sci.*, (1997) 80: 2035-2044.
Kung, et al., Effects of a Live Yeast Culture and Enzymes on in Vitro Ruminal Fermentation and Milk Production of Dairy Cows, *J Dairy Sci.*, (1997) 80: 2045-2051.
Shaver, et al., Effect of Dietary Yeast Culture on Milk Yield, Composition, and Component Yields at Commercial Dairies, *Prof. Anim. Scientist*, (1997) 13: 204-207.
Rees, Tomas, The Development of a Novel Antifungal Silage Inoculant, http://www.brighton73.freeserve.co.uk/tomsplace/scientific/phd/Introduction/phd-intr.htm; (1997).
Degrassi, et. al., Purification and Characterization of an Acetyl Xylan Esterase from *Bacillus pumilus*, *Appl. Environ Microbiol*, (1998), 64(2): 789-792.
Robinson, et al., Effect of Yeast Culture (*Saccharomyces cerevisiae*) on Adaptation of Cows to Postpartum Diets and on Lactational Performance, *J. Anim. Sci.* (1999), 77:988-999.
Wohlt, et al., Effect of Yeast on Feed Intake and Performance of Cows Fed Diets Based on Corn Silage During Early Lactation, *J Dairy Sci* (1998), 81: 1345-1352.
Nsereko, et al., Effects of fungal enzyme preparations on hydrolysis and subsequent degradation of alfalfa hay fiber by mixed rumen microorganisms in vitro, *Anim. Feed Sci Technol*, (2000), 88:153-170.
Tricarico, et al., Contribution of an acetyl esterase containing enzyme preparation to the action of exogenous enzyme supplements for ruminants, *J. Dairy Sci.*, (2001) 84:283.
Yang, C.-M. J., Response of Forage Fiber Degradation by Ruminal Microorganisms to Branched-Chain Volatile Fatty Acids, Amino Acids, and Dipeptides, *J. Daily Sci.*, (2001), 85:1183-1190.
Teagasc Directory of Silage Additives, 2004, http://www.teagasc.ie/publications/2004/Silage_Additives_List_2004.pdf, (2004).
Forage Inoculant 9 Trillion Plus 5 oz., http://store.yahoo.com/animalmedicstore/forin9trilpl.html, (2004).
Pro-Store at., http://www.agrinutrition.com/prostoreat.shtml, (2004).
Muck, Richard, Inoculants for Legume-Grass Silage, http://www.uwex.edu/ces/crops/uwforage/Inoculating_Legume_Grass_Silage.htm, (2004).

* cited by examiner (Continued)

*Primary Examiner*—David M. Naff
*Assistant Examiner*—Debbie K Ware
(74) *Attorney, Agent, or Firm*—Kathryn K. Lappegard

(57) ABSTRACT

Acetyl esterase producing bacterial strains or functional mutants thereof and methods of using acetyl esterase producing bacterial strains as forage additives are disclosed.

1 Claim, No Drawings

ACETYL ESTERASE PRODUCING STRAINS AND METHODS OF USING SAME

CROSS-REFERENCE TO RELATED APPLICATIONS

This application is a divisional of U.S. Ser. No. 10/947,865, filed on Sep. 23, 2004, which claims the benefit of U.S. Provisional Application No. 60/505,521, filed on Sep. 23, 2003, both of which are herein incorporated by reference in their entirety.

TECHNICAL FIELD

Organisms that produce acetyl esterase and methods of using same to enhance plant dry matter and fiber digestion in animals, as well as, enhance the preservation of the ensiled forage are disclosed.

BACKGROUND OF INVENTION

The plant cell wall is a complex structure consisting of different polysaccharides, the major components being cellulose, hemicelluloses and pectins. The resistance of the plant cell wall to digestion presents significant challenges in the animal production industry. Presently, in livestock agriculture while a high-forage diet is desirable, it does not currently satisfy the demands of modern animal production. Fiber digestion is a limiting factor to dairy herd milk yield and composition, and to beef production in beef operations feeding a high forage diet, and hence restricts profitability of farmers. Enhancing fiber digestion has a dual impact: 1) the animal eats more due to a reduced gut fill and therefore produces more, and 2) the animal gets more out of what it eats since the fiber is more digestible. Ultimately, this should increase milk yield, in dairy cows, and beef production in forage fed animals. Farmers either have to put up with a lower level of feed digestibility and hence productivity, or they can use inoculants, forage additives or other amendments that improve the digestibility of feed.

Accordingly, farmers can treat ensiled feed or other animal feed with fiber degrading enzymes, originating mainly from molds, to improve digestibility of feed. In addition, there are several commercially available *Saccharomyces cerevisiae* yeast strains that when fed to cattle reportedly improve fiber digestion (Erasmus et al., (1992) *J. Dairy Sci.* 75: 3056-3065; and Wohlt et al., (1998) *J. Dairy Sci.* 81: 1345-1352). Plant tissues and fibers can be disrupted to help release nutrients by adding organisms or enzymes produced by these organisms to forage before feeding or ensiling.

For example, in U.S. Pat. No. 6,037,161, an *Aspergillus* acetyl esterase nucleic acid sequence is described which encodes an enzyme with activity towards acetylated xylans that may be used to modify plant materials for enhanced nutrient availability. However, these methods can be difficult and expensive to practice because recombinant technologies, fermentations, and chromatographic processes are required. In addition, the resultant enzyme has a narrow range of substrates and can fail to effectively release nutrients from many plant materials.

Generally, for an animal to make efficient use of the feed it consumes, the energy demands of the microorganisms in the digestive tract must be met and synchronized with the availability of plant proteins. A lack of synchrony will lead to a) proteins and other nutrients being poorly utilized in the digestive tract, b) a loss of nitrogen, in urine and feces and c) a need to feed excessive amounts of protein concentrates as supplements to the diet. The use of organisms and enzymes can improve or enhance the value of the feed animals receive and the performance of the animals. For example, WO 92/10945 discloses such a combination for use in enhancing the value of prepared silage. WO 93/13786 and WO 96/17525 relate to the enhancement of animal performance using microorganisms, while WO 93/13786 refers to a species of *Lactobacillus*.

Silage can be spoiled when aerobic organisms, such as some yeast and molds, propagate in the stored feed. For example, silage can be damaged by air leaks in a silo or when air is introduced while farmers are removing part of the silage. In the presence of oxygen, yeasts, molds, and aerobic bacteria can consume nutrients, and release unpleasant or toxic metabolites. This elevated aerobic microbe activity has been considered undesirable since it often results in aerobic spoilage of silage and the consequent depletion of silage dry matter (DM) nutrition. However, some microbes, such as killer yeast (see U.S. Pat. No. 6,489,158) and *Lactobacillus buchneri* strains (see U.S. Pat. No. 6,326,037) can beneficially inhibit growth of spoilage microbes thereby stabilizing nutrient value of ensiled plant materials. A further method to reduce this problem is to inoculate the silage with a fast growing microbe, such as *Lactobacillus* species, which release organic acids to lower the silage pH and inhibit growth of spoilage organisms.

SUMMARY OF INVENTION

It has now been found that acetyl esterase producing bacterial strains or functional mutants thereof are suitable for use as a silage inoculant for improving fiber digestibility.

Further it has been found that plant fiber digestion in an animal is enhanced by feeding the animal fibrous plant material treated with an effective amount of an acetyl esterase containing composition, wherein the acetyl esterase containing composition is derived from a acetyl esterase producing bacterial strain or functional mutant thereof.

Embodiments of the present invention provide methods of treating animal feed or silage with the acetyl esterase producing bacterial strains disclosed herein, as well as the treated animal feed or silage itself. Methods of improving animal performance by feeding the inoculated animal feed or silage are also provided.

DETAILED DESCRIPTION OF INVENTION

Before describing the embodiments of the present invention in detail, it is to be understood that this invention is not limited to particular compositions or methods of improving digestibility of ensiled forage, which can, of course, vary. It is also to be understood that the terminology used herein is for the purpose of describing particular embodiments only, and is not intended to be limiting.

As used in this specification and the appended claims, the singular forms "a," "an" and "the" can include plural referents unless the content clearly indicates otherwise. Thus, for example, reference to "a component" can include a combination of two or more components; reference to "feed" can include mixtures of feed, and the like.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. In describing and claiming the embodiments of the present invention, the following terminology will be used in accordance with the definitions set out below.

The term "digestibility," as used herein, refers to the ability to derive soluble nutrients from a feed plant material. Digestibility can be determined, e.g., by analyses that provide assay data indicating the amount of feed residue remaining in a digestion and/or by analyses that provide assay data indicating the amount of nutrients released from feed in a digestion.

The term "nutrient availability," as used herein, refers to the amount of soluble nutrients made available in a digestion. Nutrient availability can be a measure of feed digestibility. Feed plant material nutrient availability can be determined by assay of: feed plant materials, feed plant materials treated with compositions of the invention, ensiled feed plant materials, in vitro digested feed plant materials, in situ digested feed plant materials, and/or the like. Assays for measurement of nutrient availability can include, e.g., gas chromatography, sugar assays, amino acid assays, free fatty acid assays, volatile fatty acid assays, carbohydrate assays, and/or the like.

The term "inoculation," as used herein, refers to introduction of viable microbes to media or feed plant material.

The term "plant material," as used herein, refers to material of plant origin. Feed plant material is plant material intended to be fed to an animal.

As used herein, "acetyl esterase" includes one or more enzymes that hydrolyze p-nitrophenyl acetate to form p-nitrophenol and acetic acid. Thus, the present invention contemplates the use of one or more esterases with activity for p-nitrophenyl acetate as animal feed supplements to improve the digestion of a high fiber diet. Enzymes classified as acetyl esterases include, without limitation, xylan acetyl esterases, mannan acetyl esterases and rhamnogalacturonan acetyl esterases.

The term "conditioned media," as used herein, refers to media of the embodiments of the invention in which acetyl esterase producing bacterial species have been grown. Such media are said to be conditioned, e.g., by the release of metabolites, inhibitors, and/or enzymes into the media from the acetyl esterase producing bacteria.

Units, prefixes, and symbols may be denoted in their SI accepted form. Numeric ranges recited within the specification are inclusive of the numbers defining the range and include each integer within the defined range.

As used herein, "functional mutant" means a bacterial strain directly or indirectly obtained by genetic modification of, or using, the referenced strain(s) and retaining at least 50% of the activity of a control silage using the referenced strain. The genetic modification can be achieved through any means, such as but not limited to, chemical mutagens, ionizing radiation, transposon-based mutagenesis, or via conjugation, transduction, or transformation using the referenced strains as either the recipient or donor of genetic material.

As used herein, "isolated" means removed from a natural source such as from uninoculated silage or other plant material.

As used herein, "purified" means that a bacterial species or strain is substantially separated from, and enriched relative to: yeasts, molds, and/or other bacterial species or strains found in the source from which it was isolated.

As used herein, "animal performance" means the yield of meat, milk, eggs, offspring, or work.

The term "silage" as used herein is intended to include all types of fermented agricultural products such as grass silage, alfalfa silage, wheat silage, legume silage, sunflower silage, barley silage, whole plant corn silage (WPCS), sorghum silage, fermented grains and grass mixtures, etc.

As used herein, "pre-ensiled plant material" means grasses, maize, alfalfa and other legumes, wheat, sorghum, sunflower, barley and mixtures thereof. All of which can be treated successfully with the inoculants of the embodiments of the present invention. The inoculants of the embodiments of the present invention are also useful in treating high moisture corn (HMC).

An embodiment of the invention is a composition for use as a silage inoculant comprising an acetyl esterase producing bacterial strain or a functional mutant thereof and a suitable carrier. Suitable acetyl esterase producing bacterial strains or functional mutants thereof include *Bacillus* strains. Suitable acetyl esterase producing *Bacillus* strains or functional mutants thereof include *Bacillus subtilis* and *Bacillus pumilus* strains. Suitable acetyl esterase producing *Bacillus subtilis* and *Bacillus pumilus* strains include *Bacillus subtilis*, strain BS62, deposited as Patent Deposit No. NRRL B-30763, *Bacillus subtilis*, strain BS116, deposited as Patent Deposit No. NRRL B-30764, *Bacillus subtilis*, strain BS5482, deposited as Patent Deposit No. NRRL B-30765, *Bacillus pumilus*, strain BP5295, deposited as Patent Deposit No. NRRL B-30766, *Bacillus pumilus*, strain BP5579, deposited as Patent Deposit No. NRRL B-30767, *Bacillus subtilis*, strain BS5752, deposited as Patent Deposit No. NRRL B-30768, and mixtures thereof.

In an embodiment of the invention the composition contains from about $10^1$ to about $10^{10}$ viable organisms of the acetyl esterase producing bacterial strain or functional mutant thereof per gram of a pre-ensiled plant material. In a further embodiment of the invention the composition contains from about $10^2$ to about $10^7$ viable organisms of the acetyl esterase producing bacterial strain or functional mutant thereof per gram of a pre-ensiled plant material. In yet a further embodiment the composition contains from about $10^3$ to about $10^6$ viable organisms of the acetyl esterase producing bacterial strain or functional mutant thereof per gram of a pre-ensiled plant material.

Suitable carriers are either liquid or solid and are well known by those skilled in the art. For example, solid carriers may be made up of calcium carbonate, starch, cellulose and combinations thereof.

An embodiment of the invention is a biologically pure culture of *Bacillus subtilis*, strain BS62, deposited as Patent Deposit No. NRRL B-30763. A further embodiment of the invention is a biologically pure culture of *Bacillus subtilis*, strain BS116, deposited as Patent Deposit No. NRRL B-30764. Another embodiment of the invention is a biologically pure culture of *Bacillus subtilis*, strain BS5482, deposited as Patent Deposit No. NRRL B-30765. An additional embodiment of the invention is a biologically pure culture of *Bacillus pumilus*, strain BP5295, deposited as Patent Deposit No. NRRL B-30766. A further embodiment of the invention is a biologically pure culture of *Bacillus pumilus*, strain BP5579, deposited as Patent Deposit No. NRRL B-30767. Another embodiment of the invention is a biologically pure culture of *Bacillus subtilis*, strain BS5752, deposited as Patent Deposit No. NRRL B-30768.

A deposit of the following microorganisms was made on Sep. 1, 2004 with the Agricultural Research Service (ARS) Culture Collection, housed in the Microbial Genomics and Bioprocessing Research Unit of the National Center for Agricultural Utilization Research (NCAUR), under the Budapest Treaty provisions. The strains were given the indicated accession numbers. The address of NCAUR is 1815N. University Street, Peoria, Ill., 61604. *Bacillus subtilis*, strain BS62, NRRL B-30763, *Bacillus subtilis*, strain BS116, NRRL B-30764, *Bacillus subtilis*, strain BS5482, NRRL B-30765, Bacillus pumilus, strain BP5295, NRRL B-30766, *Bacillus pumilus*, strain BP5579, NRRL B-30767, *Bacillus subtilis*, strain BS5752, NRRL B-30768. Applicant(s) will meet all the requirements of 37 C.F.R. §1.801-1.809, including providing an indication of the viability of the sample when the deposit is made. Each deposit will be maintained without restriction in the ARS Depository, which is a public depository, for a period of 30 years, or 5 years after the most recent request, or for the enforceable life of the patent, whichever is longer, and will be replaced if it ever becomes nonviable during that period. The deposits will irrevocably and without restriction or condition be available to the public upon issuance of a patent. However, it should be understood that the availability of a deposit does not constitute a license to practice the subject invention in derogation of patent rights granted by government action.

A method for treating pre-ensiled plant material to enhance the digestibility of the resulting silage by adding to the pre-ensiled plant material a digestibility enhancing amount of a composition containing an acetyl esterase producing bacterial strain or a functional mutant thereof of is also disclosed. Suitable pre-ensiled plant materials include grasses, maize, alfalfa and other legumes, wheat, sorghum, sunflower, barley and mixtures thereof.

An embodiment of the invention is a method for enhancing plant fiber digestion in an animal by feeding a fibrous plant material treated with an effective amount of a acetyl esterase-containing composition to the animal, wherein the acetyl esterase is derived from a acetyl esterase producing bacterial strain or a functional mutant thereof. Suitable acetyl esterase producing bacterial strains or functional mutants thereof include *Bacillus* strains. Suitable *Bacillus* strains or functional mutants thereof include *Bacillus subtilis* and *Bacillus pumilus* strains. Suitable *Bacillus subtilis* and *Bacillus pumilus* strains include *Bacillus subtilis*, strain BS62, deposited as Patent Deposit No. NRRL B-30763, *Bacillus subtilis*, strain BS116, deposited as Patent Deposit No. NRRL B-30764, *Bacillus subtilis*, strain BS5482, deposited as Patent Deposit No. NRRL B-30765, *Bacillus pumilus*, strain BP5295, deposited as Patent Deposit No. NRRL B-30766, *Bacillus pumilus*, strain BP5579, deposited as Patent Deposit No. NRRL B-30767, *Bacillus subtilis*, strain BS5752, deposited as Patent Deposit No. NRRL B-30768, and mixtures thereof.

The composition that is fed to the animal has been treated with an effective catalytic amount of the acetyl esterase producing bacterial strain or functional mutant thereof as is readily determinable by those skilled in the art in animal husbandry. Animals that are benefited by embodiments of the present invention are mammals and birds, including but not limited to ruminant, equine, bovine, porcine, caprine, ovine and avian species, e.g., poultry.

An embodiment of the invention is a substantially purified strain of a bacterium selected from the group consisting of *Bacillus subtilis*, strain BS62, deposited as Patent Deposit No. NRRL B-30763, *Bacillus subtilis*, strain BS116, deposited as Patent Deposit No. NRRL B-30764, *Bacillus subtilis*, strain BS5482, deposited as Patent Deposit No. NRRL B-30765, *Bacillus pumilus*, strain BP5295, deposited as Patent Deposit No. NRRL B-30766, *Bacillus pumilus*, strain BP5579, deposited as Patent Deposit No. NRRL B-30767, *Bacillus subtilis*, strain BS5752, deposited as Patent Deposit No. NRRL B-30768, and mixtures thereof.

EXAMPLES

Embodiments of the present invention are further defined in the following Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

Example 1

Testing of Bacillus Strains for Production of Acetyl Esterase Activity

A total of about 5500 strains from one of the Microbial Culture Collections of Pioneer Hi-Bred International Inc., Des Moines, Iowa were screened for acetyl esterase activity using 4-nitrophenyl acetate (pNP-acetate; Sigma Chemical Co., St. Louis Mo.) as the substrate.

A standard assay was used whenever a small number of strains were tested for activity. For the standard assay, *bacillus* strains were streaked from freezer vials onto Tryptic soy agar (TSA, DIFCO, Becton, Dickinson and Co., Sparks, Md.) and incubated at 30° C. for 72 h. Cultures were inoculated directly from the TSA plates in to 10 mL of Tryptic soy broth (TSB) and grown at 30° C. for 24 h on a roller drum. Freshly prepared whole plant corn broth (WPCB; 10 mL) was then inoculated with TSB grown cultures and incubated at 30° C. for 48-72 h on a roller drum. WPCB was prepared by suspending whole plant corn (WPC) (ground to pass a 1 mm screen) in distilled (D) $H_2O$ (3.4%; w/v), autoclaving (sterilizing) the mixture (121° C., 15 min) and then cooling the mixture to room temperature prior to use. An uninoculated WPCB (control) treatment was included at all times in order to verify that acetyl esterase activity was the result of inoculation. Culture supernatants were collected by centrifugation and freeze-dried or assayed immediately for acetyl esterase activity as described below.

For the high throughput screening of about 5500 strains, strains were inoculated into 96 well microtitre plates containing 200 μL of TSB per well and incubated on a plate shaker at 150 rpm for 24 h at 30° C. Sterile WPCB was dispensed into a 96 deep well filtration microtiter plate (Millipore Cooperation, Billerica, Mass.) and each well was then inoculated with 20 μL of the 24 h TSB cultures using an 8-channel micropipette. WPCB filtration microtiter plates were incubated at 30° C. for 72 h, with shaking at 150 rpm, and then filtered by vacuum using a Millipore vacuum manifold (Millipore Cooperation, Billerica, Mass.). The culture filtrates were collected and assayed for acetyl esterase activity as described below.

Acetyl esterase activity was measured using a modification of the procedures described by Huggins and Lapides (1947) (J. Biol. Chem. 170: 467-482.) and Williams and Withers, (1981) (J. Appl. Bacteriol. 51 375-385). Briefly, a standard stock solution of p-nitrophenol (10 mM, in 0.05 M citrate phosphate buffer, pH 6.0) was prepared, dispensed into 1 mL aliquots and these were kept frozen, and utilized individually when required. The assays were performed in 96 well microtitre plate format as shown in Table 1.

TABLE 1

Typical microtiter plate well assignments for acetyl esterase activity assay:

| ITEM | Row and well numbers |
|---|---|
| WPCB control[1] | Row A wells 1-3. |
| Buffer control[2] | Row B wells 1-3. |
| Standards #1-6[3] | Row C-H wells 1-3. |
| Enzyme positive control[4] | Row H wells 10-12. |
| BACILLUS TEST SAMPLES | Remaining wells in triplicate |

[1]Whole plant corn broth
[2]Citrate phosphate buffer (0.05 M; pH 6.0)
[3]See Table 2 for preparation of standards
[4]Pectinex 3X L (Novozymes North America Inc., Franklinton. NC)

A standard curve was prepared first by diluting a stock standard ten fold in 0.05 M (pH 6) citrate phosphate buffer (buffer) to produce a working standard, and then by substituting working standard solution with buffer as shown in Table 2.

TABLE 2

Preparation of standard curve for acetyl esterase assay

| Standard | Working standard (µL) | Buffer[1] |
|---|---|---|
| 1 | 5 | 195 |
| 2 | 10 | 190 |
| 3 | 15 | 185 |
| 4 | 30 | 170 |
| 5 | 45 | 155 |
| 6 | 60 | 140 |

[1]Citrate phosphate buffer (0.05 M; pH 6.0)

The final incubation volume in each well was 200 µL. Forty microliters of buffer or WPCB were dispensed in to the microtitre plate well as illustrated in Table 1. Buffer, 160 µL, was then dispensed into the wells containing WPCB to account for background WPCB absorbance at 405 nm.

Forty (40) microliters of a 1:500 dilution (in buffer) of Pectinex 3X L (Novozymes, North America Inc, Franklinton, N.C.) was dispensed as illustrated in Table 1. Pectinex 3X L was used as a positive control for the acetyl esterase assay. Forty (40) microliters of culture supernatants prepared as described above were then dispensed in the microtitre plate wells as illustrated in Table 1. The substrate solution was prepared by dissolving 18.11 mg of 4-nitrophenyl acetate in 710 µL of dimethylsulphoxide and then this solution was diluted to 100 mL in buffer. Using an 8-channel micropipette, 160 µL of substrate were dispensed into the buffer control wells and 160 µL of substrate were dispensed into wells 4-12 (see Table 1). A time zero absorbance reading (405 nm; Vmax Kinetic Microplate Reader, Molecular Devices, Menlo Park, Calif.) was taken immediately after addition of substrate and the plates then incubated at 30° C.

The plates were read again after 30 min. and cultures that had a corrected absorbance of more that 0.09 (about 160 strains) were deemed to be acetyl esterase producers of interest. Under these assay conditions the actual range in absorbance (405 nm) for the producers of interest was 0.091 to 0.889. All bacillus strains incorporated in the proceeding examples belonged to this subset of about 160 acetyl esterase producing strains of interest.

For the freeze dried bacillus culture supernatants described in Examples 2 and 3, freeze-dried material was diluted in de-ionized distilled water and acetyl esterase activities were determined following a 60 min. incubation. For strains used as inoculants for silage (*Bacillus subtilis*, strain BS62, deposited as Patent Deposit No. NRRL B-30763, *Bacillus subtilis*, strain BS5482, deposited as Patent Deposit No. NRRL B-30765, *Bacillus pumilus*, strain BP5295, deposited as Patent Deposit No. NRRL B-30766, *Bacillus pumilus*, strain BP5579, deposited as Patent Deposit No. NRRL B-30767, *Bacillus subtilis*, strain BS5752, deposited as Patent Deposit No. NRRL B-30768) in Examples 4, 5 and 6, acetyl esterase activities were determined on supernatants harvested from 24 h TSB cultures. Concentrations of protein in the supernatant of these cultures were then determined using the method of Bradford (Bradford, M, (1976) Anal. Biochem. 72 248-254). Specific acetyl esterase activities of BP5295, BP5579, BS62, BS116, BS5482, and BS5752 were 94.6, 82.6, 28.0, 45.2, 9.8 and 69.6 µmol pNP g protein$^{-1}$ min$^{-1}$, respectively.

Example 2

Effects of Culture Supernatants of Acetyl Esterase Producing Bacillus on Ruminal Digestibility of Corn SILAGE In Vitro Proprietary *Bacillus* strains SB7.85 and X450 were selected for an experiment to determine the effects of a crude enzyme rich WPCB culture supernatant on digestibility of corn silage. Strains were streaked from freezer vials onto TSA (DIFCO, Becton, Dickinson and Co., Sparks, Md.) plates and incubated at 30° C. for 72 h. Cultures were then inoculated directly from the TSA plates in to 10 mL of TSB and grown at 30° C. for 24 h.

Following incubation, 10 mL of TSB grown cultures was poured directly into 100 mL of freshly prepared WPCB. WPCB was prepared as described in Example 1. An additional treatment consisting of 100 mL of uninoculated WPC broth was included as an uninoculated control and treated in exactly the same way as the cultures. Inoculated and uninoculated WPCB was incubated at 30° C. for 24 h and then transferred into ten 100 mL WPCB prepared as described above, and further incubated at 30° C. for 72 h. Supernatants were collected following centrifugation (26 000×g, 4° C.; 30 min.), freeze-dried, and then assayed for acetyl esterase activity as described in Example 1. Freeze dried supernatants were then stored in zip lock plastic bags at 4° C. Acetyl esterase activities of freeze dried supernatants from X-450 and SB7.85 were 1.79 and 1.20 µmol pNP g supernatant$^{-1}$ min$^{-1}$, respectively. WPCS was obtained from a bunker silo at the Pioneer Livestock Nutrition Center (PLNC), Sheldahl, Iowa, dried and ground to pass an 8 mm screen. For each treatment, WPCS (5 g) was weighed into aluminum foil trays and spread evenly across the bottom of the trays. Fifty-five ((55), low), 110 (medium) and 550 (high) mg of freeze dried supernatants harvested from inoculated (SB7.8 and X-450) and uninoculated (control) broth cultures were re-suspended in 3 mL of distilled water in a 15 mL falcon tube, and mixed thoroughly to provide a uniform solution. These solutions were then sprayed onto the silage, with regular and thorough mixing by use of a spatula, during and after application. Treated silage was left at room temperature for 24 h and then dried to constant weight in a forced air oven at 62° C.

For the determination of effects on in vitro ruminal fermentation, 5 replicates of untreated (control) and treated silage (approximately 300 mg) were accurately weighed into 100 mL serum vials (VWR Int., West Chester, Pa.). In vitro ruminal digestion studies were performed using a modification of the method of Pell and Schofield (1993) (J. Dairy Sci. vol 76 No 4, 1063-1073). Briefly, twenty-four (24) ml of the anaerobic incubation solution (phosphate-bicarbonate buffer and reducing solution; 39° C.) of Goering, and Van Soest (Goering, H. K. and P. J. Van Soest (1970); Forage fiber analyses Handbook No. 379. ARS-USDA, Washington, D.C.), was added to the serum vials containing the silage under a stream of oxygen free $CO_2$. The serum vials were sealed with butyl septa (Geo-Microbial Technologies, Inc., Ochelata, Okla.) and then crimped with aluminum seals (VWR Int., West Chester, Pa.) and placed in a 39° C. incubator. Ruminal fluid obtained from two (2) steers fed a diet of whole plant corn silage (WPCS) for more than two (2) weeks prior to experimentation, was strained through two (2) layers of cheese cloth, combined to create one solution and then maintained under a stream of oxygen free $CO_2$. Strained rumen fluid, 6 mL, was then added to each of the serum vials at 39° C. under a stream of oxygen free $CO_2$ and the mixtures incubated, with shaking (54 RPM) at 39° C. for 24 h. Blanks consisting of serum vials with no silage but containing all the other incubation mixture components were included as controls to account for non-silage derived DM and volatile fatty acid (VFA).

On termination of the incubation, a 1 mL aliquot was collected from each serum vial, processed and then analyzed for VFA concentrations using gas chromatography as is known in the art. The rest of the serum vial contents were individually filtered through a pre-weighed piece of nitrogen free nylon (approximately 10 cm by 10 cm; 40 microns + or − 15 pore size; Ankom Technology Corp., Fairport, N.Y.) using a Buchner flask attached to a vacuum source. The nylon pieces, now holding the incubation mixture residue for each sample, were folded over, dried to a constant weight at 62° C., and then reweighed.

Dry matter disappearance (DMD) (%) was determined as the difference between the original silage weight and the weight of the residue from the serum vials, divided by the original silage weight and then multiplied by 100. The vials containing no silage were also filtered and weighed in the same manner in order to correct silage-containing vials for the DM arising from the rumen fluid only.

WPCS treated with supernatants prepared from SB7.85 and X-450 WPCB cultures had higher in vitro dry matter digestibility values than control silages, which had been treated with supernatants from uninoculated WPCB (Tables 3 and 4). For X-450, this effect was only noted at the middle application level (110 mg/5 g silage) but for SB7.85, all doses employed in the study increased DMD (Table 3).

VFA concentrations produced from the WPCS treated with acetyl esterase containing *bacillus* supernatants were higher than the corresponding concentrations derived from digestion of WPCS treated with uninoculated supernatants, reflecting the enhanced DMD values observed (Tables 3 and 4).

TABLE 3

Effects of applying acetyl esterase containing *Bacillus* culture supernatants to field grown WPCS on in vitro ruminal DMD (%), Gas (mL/g silage) and VFA (mg/g) production from field grown WPCS.

| Dose | Treatment | DMD (%) | Gas (mL/g) | Ruminal VFA produced (mg/g WPCS) | | | | |
|---|---|---|---|---|---|---|---|---|
| | | | | Acetate | Propionate | Butyrate | Valerate | Total VFA |
| Low[1] | Control | 64.8 | 204 | 181 | 94.1 | 63.6 | 5.33 | 344 |
| | X-450 | 63.1 | 179** | 179 | 91.6 | 62.1 | 5.25 | 338 |
| | SB7.85 | 67.3* | 211 | 182 | 98.7 | 64.5 | 6.68 | 352 |
| Medium[2] | Control | 65.4 | 202 | 178 | 90.0 | 57.8 | 3.69 | 329 |
| | X-450 | 67.8* | 221** | 181 | 97.4** | 61.6 | 6.84* | 346 |
| | SB7.85 | 67.1 | 224** | 187* | 100** | 65.3 | 7.44* | 360** |
| High[3] | Control | 63.6 | 214 | 176 | 90.5 | 56.4 | 5.05 | 328 |
| | X-450 | 64.3 | 215 | 186* | 102** | 61.8 | 7.72 | 359** |
| | SB7.85 | 68.5** | 227** | 187* | 106** | 70.9** | 8.11* | 372** |
| SE[4] | | 0.76 | 3.13 | 3.30 | 2.2 | 3.07 | 1.04 | 7.68 |

[1]55 mg freeze dried supernatant/5 g whole plant corn silage.
[2]110 mg freeze dried supernatant/5 g whole plant corn silage.
[3]550 mg freeze dried supernatant/5 g whole plant corn silage.
*, **significantly different from control at P < 0.05 and P < 0.01, respectively.
Means are least square means.
[4]SE—standard error.

TABLE 4

Overall treatment effects of applying acetyl esterase containing *Bacillus* culture supernatants to WPCS on in vitro ruminal DMD (%), Gas (mL/g silage) and VFA production (mg/g) from field grown WPCS at 48 h.

| Treatment | DMD (%) | Gas (mL/g) | Ruminal VFA produced (mg/g WPCS) | | | | |
|---|---|---|---|---|---|---|---|
| | | | Acetate | Propionate | Butyrate | Valerate | Total VFA |
| Control | 64.6 | 207 | 179 | 91.4 | 59.2 | 4.69 | 334 |
| X-450 | 65.1 | 205 | 182 | 96.9* | 61.8* | 6.60* | 347* |
| SB7.85 | 67.8** | 221** | 186** | 102** | 66.9** | 7.41** | 361** |
| SE[1] | 0.42 | 1.74 | 1.83 | 1.22 | 1.71 | 0.578 | 4.28 |
| Trt x Dose | ** | ** | NS[2] | ** | NS | NS | NS |

*, **Significantly different from control at P < 0.05 and P < 0.01, respectively.
Means are least square means.
[1]SE - standard error.
[2]NS - not significant.

As shown in the above Tables the application of acetyl esterase containing supernatants derived from *Bacillus* strains to ensiled WPCS enhances digestion of the treated WPCS.

Example 3

Effects of Culture Supernatants of Acetyl Esterase Producing Bacillus on Ruminal Digestibility of Corn Silage In Situ

*Bacillus* strains BP5295 (NRRL B-30766), BP5294, and proprietary strains 5313 and SB7.85 were streaked from freezer vials on to TSA (DIFCO, Becton, Dickinson and Co., Sparks, Md.) plates and incubated at 30° C. for 72 h. Cultures were then inoculated as per the protocol given in Example 2 for the inoculation and growth of the *Bacillus* strains SB7.85 and X450. Inoculated broths were then transferred by adding 5 mL of culture into each of sixty 100 mL WPCB. Cultures were incubated at 30° C. for 72 h and the supernatants were collected following centrifugation (26 000×g, 4° C.; 30 min.), freeze-dried, and then assayed for acetyl esterase activity as described in Example 1. Freeze dried supernatants were then stored in zip lock plastic bags at 4° C. Acetyl esterase activities of freeze dried supernatants from BP5295, BP5294, 5313 and SB7.85 were 26.9, 9.4, 5.3 and 1.20 μmol pNP g supernatant$^{-1}$ min$^{-1}$, respectively.

WPCS was obtained from a bunker silo, dried and ground to pass an 8 mm screen. WPCS (150 g) was weighed into each of twelve (12) large aluminum foil trays and spread evenly across the bottom of the trays.

Freeze dried supernatants were re-suspended in 100 mL of distilled water at three (3) concentrations (1.32, 5.23 and 10.56 g) and mixed thoroughly to provide a uniform solution. These solutions were then sprayed onto the silage, with regular and thorough mixing by use of a spatula, during and after application. Treated silage was left as at room temperature for 24 h and then dried to constant weight in forced air oven at 62° C.

Both micro (5.5 cm by 5.5 cm; 40 microns + or − 15; Ankom Technology Corp., Fairport, N.Y.) and macro in situ bags (20 cm by 24 cm; 40 microns + or − 15; Ankom Technology Corp., Fairport, N.Y.) were used for the ruminal determination of digestibility.

For the experiments performed using the micro in situ bags, DMD analysis was concluded by incubating 0.5 g of dried ground silage in three (3) ruminally fistulated steers, which had been fed and adapted to a 100% WPCS diet for two (2) weeks prior to experimentation. For each treatment, two (2) repetitions were incubated in each of the 3-ruminally fistulated steers for 24, 48 and 72 h.

For experiments carried out using the macro in situ bags, DMD was determined as described above but only following a 48 h ruminal incubation of the medium level (5.23 g/150 g silage) only. Neutral detergent fiber (NDF) and acid detergent fiber (ADF) concentrations of the silage before and after the 48 h ruminal incubation were determined using the Ankom Fiber Analyzer (Ankom Technology Corp., Fairport, N.Y.).

Original silage weights for each silage-containing micro in situ bag were corrected for the A-fraction to give a corrected starting weight. The A-fraction was determined as the loss in silage DM when sealed silage-containing micro in situ bags were immersed in water (15° C.) for 15 min., washed gently for 2 min. on a slow cycle in a washing machine and then dried to constant weight at 62° C. Digestion coefficients for silage NDF (NDFD %) and ADF (ADFD %) were determined as the difference in NDF or ADF concentration before and after ruminal incubation divided by the concentration of NDF or ADF before ruminal incubation multiplied by 100.

WPCS treated with supernatants prepared from BP5294, BP5295, 5313 and SB7.85 WPC cultures had higher in vitro dry matter digestibility values than control silages and these effects were most noted after 48 and 72 h of ruminal incubation, at the medium and high application levels of application (Table 5).

TABLE 5

EFFECTS OF APPLYING ACETYL ESTERASE CONTAINING *BACILLUS* CULTURE SUPERNATANTS TO WPCS ON IN SITU DMD (MICRO BAGS)

| | | Incubation Period (h) | | |
|---|---|---|---|---|
| Treatment | Dose | 24 | 48 | 72 |
| Control | — | 42.6 | 52.1 | 61.9 |
| BP5294 | Low[1] | 44.4 | 57.9 | 63.3 |
| | Medium[2] | 49.8 | 60.2* | 68.1** |
| | High[3] | 44.8 | 59.4* | 65.3* |
| BP5295 | Low | 41.1 | 52.4 | 62.5 |
| | Medium | 44.3 | 55.0 | 65.0 |
| | High | 41.1 | 55.4 | 65.3 |
| 5313 | Low | 35.4 | 55.3 | 62.3 |
| | Medium | 42.7 | 54.7 | 66.2* |
| | High | 44.3 | 56.4 | 66.5* |
| SB7.85 | Low | 42.2 | 57.6 | 65.1 |
| | Medium | 45.7 | 58.6 | 64.1 |
| | High | 47.2 | 58.4 | 67.4** |
| SE[4] | | 2.05 | 1.64 | 0.99 |

[1]1.32 g freeze-dried supernatant per 150 g whole plant corn silage
[2]5.23 g freeze-dried supernatant per 150 g whole plant corn silage
[3]10.56 g freeze-dried supernatant per 150 g whole plant corn silage
[4]SE, Standard error.
*, **Significantly different from control at P < 0.05 and P < 0.01, respectively.

Table 6 shows that NDFD levels were higher for WPCS treated with BP5294, BP5295 and 5313, and all treatments had higher levels of ADFD than the untreated control.

TABLE 6

EFFECTS OF APPLYING ACETYL ESTERASE CONTAINING *BACILLUS* CULTURE SUPERNATANTS TO WPCS (5.23 G/150 G) ON IN SITU DM, NDF AND ADF DISAPPEARANCE AT 48 H (MACRO BAGS)

| | Digestion coefficients | | |
|---|---|---|---|
| Treatment | DMD | NDFD | ADFD |
| Control | 57.1 | 49.4 | 51.5 |
| BP5294 | 61.6 | 52.2 | 57.6 |
| BP5295 | 61.9 | 56.3 | 52.2 |
| 5313 | 61.3 | 52.5 | 56.7 |
| SB7.85 | 59.1 | 49.4 | 53.3 |
| SE | 2.00 | 2.32 | 2.75 |

These results show that application of acetyl esterase containing supernatants derived from *bacillus* strains BP5294, BP5295, SB7.85 and 5313 improved in situ DM and fiber digestibility, and that this effect was most pronounced after 48-72 h of ruminal incubation.

Example 4

Effects of Inoculation with Acetyl Esterase Producing *Bacillus pumilus* and *B. subtilis* Strains at Ensilage on In Vitro Ruminal Digestion of Corn Silage Green house (GH) grown corn plants, without tassels and ears were obtained from Pioneer Hi-bred International, Inc. greenhouses in Johnston, Iowa. The plants were chopped using a Bearcat chipper/shredder and then blended with rehydrated cracked corn kernels (3:2, respectively) to achieve a target DM of 350 g/kg. The cracked corn kernels were rehydrated by mixing with $H_2O$ (3:1, wt/vol, respectively) and leaving the mixture overnight at 4° C.

Acetyl esterase producing *Bacillus pumilus* strain BP5295 and *Bacillus subtilis* strains BS5752 and BS62 (see Example 1 for specific acetyl esterase activities of these strains) were grown overnight TSB (DIFCO, Becton, Dickinson and Co., Sparks, Md.), on a roller drum, to reach a cell count of about $1 \times 10^9$ cfu/mL. For each strain, 0.45 mL of the overnight culture was added to 0.55 mL peptone-phosphate in a microfuge tube to give $4.5 \times 10^8$ cfu/mL. This 1 mL of culture was then applied to 454 g of forage prepared as described above, to give an application rate of about $1 \times 10^6$ cfu per gram. The treatments were applied to forage as aqueous solutions, by syringe dispersion, in a total of 2.2 mL/kg$^{-1}$. The treatments were thoroughly mixed in to the forage by rolling the forage on a clean plastic sheet as they were applied to the forage.

Forage, 100 g, was ensiled, in quadruplicate for each treatment, in polyethylene packet silos, which were vacuum packed and heat sealed as described by Dennis et al. (1999) Page 87 In Proc. XII Int. Silage Conf. Swedish Univ. of Agric. Sci., Uppsala, Sweden.) using a Tilia Food Saver, Professional II model (Tilia Inc. San Francisco, Calif.). The packet silos were incubated at room temperature, and after 45 d, the silos were opened, emptied and the forage thoroughly mixed to give a uniform mass. Aqueous extracts of silage were prepared by diluting ten (10) g in ninety-nine (99) mL of sterile distilled water and agitating the mixture in a stomacher (Stomacher 400, Seward limited, London, England) for 1 min. at the medium setting. Silage pH was determined on these extracts immediately following preparation. The rest of the silages were dried to constant at 62° C. weight and then ground to pass an 8 mm screen.

For the determination of effects on in vitro ruminal fermentation, triplicate preparations of dried ground silage sample from each silo (approximately 300 mg) were accurately weighed into 100 mL serum vials (VWR Int., West Chester, Pa.). In vitro ruminal digestion studies were performed according to the protocols given in Example 2.

On termination of the incubation, a 1 mL aliquot was collected from each serum vial, processed and then analyzed for VFA concentrations using the protocols provided in Example 2.

DMD (%) was also determined according to the protocols provided in Example 2.

*Bacillus pumilus* strain 5295 and *B. subtilis* strains 5752 and 62 reduced silage pH ($P<0.05$) indicating that the strains had grown and established in the silo (Table 7). Furthermore, BP5295 and BS5752 increased DMD ($P<0.05$) demonstrating that when used as silage inoculants, both *B. subtilis* and *B. pumilus* strains were able to enhance the digestibility of corn silage. In vitro ruminal acetate, propionate and total VFA concentrations produced were higher for BP5295 and BS5752 reflecting the increases in DMD observed, although these latter differences were only statistically significant for BS5752 ($P<0.05$). Additionally both BP5295 and BS5752 increased in vitro ruminal butyric acid production ($P<0.05$).

Inoculation with BS62 tended to increase silage digestion parameters, particularly VFA production; however, for DMD, these effects were not as pronounced as those observed for BS5752 and BP5295. While not wishing to be bound by any one theory it is believed that not all *Bacillus* strains that produce acetyl esterase will necessarily improve digestibility of ensiled forage at all, or to the same extent, when used as inoculants. The degree to which successful establishment of the strain in the silo is achieved will differ between strains. Tolerances to limited concentrations of oxygen, as well as the strain's competitive ability under ensiling conditions will play a significant role in determining the efficacy of selected strains.

TABLE 7

Effects of inoculating greenhouse grown corn with acetyl esterase producing *Bacillus* strains on silage pH and in vitro ruminal digestion of the resultant silage.

| Treatment[1] | Silage pH | DMD (%) | mg produced per gram silage DM | | | | | |
|---|---|---|---|---|---|---|---|---|
| | | | Acetic Acid | Propionic Acid | Isobutyric Acid | Butyric Acid | Isovaleric Acid | Valeric Acid | Total VFA |
| Control | 3.83 | 63.2 | 140 | 117 | 0.92 | 65.08 | 0.37 | 4.52 | 327 |
| BP5295 | 3.78[a] | 65.7[a] | 143 | 123 | 1.02 | 71.3[a] | 0.51 | 4.99 | 344 |
| BS5752 | 3.78[a] | 68.4[a] | 150[a] | 128[a] | 1.01 | 69.7[a] | 0.47 | 4.96 | 354[a] |
| BS62 | 3.78[a] | 64.5 | 145 | 123 | 1.09 | 68.4 | 0.32 | 4.59 | 343 |
| SE[2] | 0.013 | 0.51 | 2.46 | 2.25 | 0.061 | 1.09 | 0.168 | 0.23 | 5.12 |

[1]Four silos were prepared for each treatment.
[2]SE, standard error.
[a]Significantly different from control at $P < 0.05$.

Example 5

Effects of Inoculation with Acetyl Esterase Producing Bacillus pumilus and B. subtilis Strains on Fermentation, Aerobic Stability and Digestibility of Silage Dry Matter and Fiber Ryegrass was a first cut, harvested at the Pioneer Livestock Nutrition Center (PLNC), Sheldahl, Iowa in June 2004. The *bacillus* strains were grown by the Quality Control and Microbial Production Group at Pioneer Hi-Bred in Johnston, Iowa, stabilized and lyophilized as is known in the art. The test strains were acetyl esterase producing (see Example 1 for specific acetyl esterase activities of these strains) *Bacillus pumilus* 5579 (BP5579), *B. pumilus* 5295 (BP5295), *Bacillus subtilis* 62 (BS62), *B. subtilis* 5752 (BS5752) and *B. subtilis* 5482 (BS5482). The ryegrass was either uninoculated (control) or inoculated with the experimental *bacillus* strains at $1\times10^6$ colony forming units/gram forage (cfu/g). The treatments were applied to forage as aqueous solutions, by syringe dispersion, and were thoroughly mixed into the forage by rolling the forage on a clean plastic sheet as the treatments were applied to the forage. For each treatment, four (4) experimental 4"×14" polyvinyl chloride (PVC) pipe silos were filled and packed at 100% packing density (approximately 230 kg DM $M^3$), using a hydraulic press. Experimental silos were fitted with rubber quick caps at each end, held tight by metal rings, and the top cap was equipped with a Bunsen valve to allow gasses to escape.

Silos were opened after 50 days of ensilage, emptied and the forage thoroughly mixed to give a uniform mass. Silage samples were allotted to the various analyses, namely: pH, DM, Total N, ammonia N, Lactate and VFA and in situ rumen digestibility. Dry matter was determined by drying to a constant weight in a forced air oven at 62° C. VFA, ammonia N and Total N (crude protein/6.25) were determined by a commercial laboratory (Dairyland Laboratories, Arcadia, Wis.) using methods known in the art. Aerobic stability assessments were concluded on individual treatment replicates using the procedure of Honig (1986) (In Proc. Of the Eurobac Conf., P. Lingvall and S. Lindgren (ed.) 12-16 Aug. 1986. Swed. Univ. of Agric. Sci. Grass and Forage Report No. 3-1990. Pp. 76-81. Uppsala, Sweden). The time (h) for silage temperature to rise 1.7° C. above ambient was recorded (ROT). The integration of the area between the actual silage temperature curve and the line drawn by ambient temperature (cumulative degree days or Cumm-DD) was calculated. Cumm-DD is a measure of total amount of heating.

Micro in situ bags (5.5 cm by 5.5 cm; 40 microns + or − 15; Ankom Technology Corp., Fairport, N.Y.) were used for all ruminal incubations. In situ DMD analysis was concluded by incubating 0.5 g dried ground silage in three (3) ruminally fistulated steers, which had been fed and adapted to a grass silage diet (95% grass silage and 5% dried rolled corn on a dry matter basis) for two (2) weeks prior to experimentation. For each silo, one (1) repetition was incubated in each of the 3-ruminally fistulated steers for 48 h; hence a total of 12 in situ bags were incubated for each treatment. The A-fraction was determined as the loss in silage DM when sealed silage-containing micro in situ bags were immersed in water (15° C.) for 15 min., washed gently for 2 min. on a slow cycle in a washing machine and then dried to constant weight at 62° C.

NDF concentrations of the silage before and after the 48 h ruminal incubation were determined using the Ankom Fiber Analyzer (Ankom Technology Corp., Fairport, N.Y.). Original silage weights for each silage-containing micro in situ bag were corrected for the A-fraction to give a corrected starting weight. Digestion coefficients for DM are presented on both the original and the A-fraction-corrected starting weights. Digestion coefficients for silage NDF (NDFD %) were determined as previously described.

Ryegrass silages were well fermented as illustrated by the terminal pH value of 4.08 for the control silages (Table 8). With the exception of BS5482, all the *bacillus* strains reduced terminal silage pH (P<0.05) and in addition, tended to improve aerobic stability of silage, although this latter effect was not statistically significant.

Interestingly, both BP5295 and BP5579 increased silage lactic acid concentrations, with little effect on acetate whereas all three (3) *B. subtilis* strains (BS62, BS5482 and BS5752) did not influence lactic acid concentrations but increased acetate concentrations.

Strains belonging to both species of Bacillus (*B. pumilus* and *B. subtilis*) increased dry matter digestibility (P<0.05). Furthermore both species improved NDFD, with the most marked effects being noted for BP5295, BP5579 and BS62 (P<0.05).

Acetyl esterase producing *Bacillus subtilis* and *B. pumilus* strains grew and established in the silo as indicated by their ability to reduce silage pH. Furthermore, *Bacillus* strains from both species (*B. pumilus* and *B. subtilis*) improved DMD and NDFD of grass silage. These data show that acetyl esterase producing *B. pumilus* and *B. subtilis* strains improved silage fermentation and dry matter and fiber digestibility when used as silage inoculants.

TABLE 8

Fermentation, aerobic stability and in situ digestibility of first cut ryegrass silages inoculated with *Bacillus* strains.

|  | Control | BP5295 | BP5579 | BS62 | BS5482 | BS5752 | SE[3] |
|---|---|---|---|---|---|---|---|
| PH | 4.08 | 4.01[a] | 4.03[a] | 4.05[a] | 4.07 | 4.01[a] | 0.005 |
| DM | 34.5 | 31.8 | 32.2 | 33.6 | 33.2 | 31.2 | 0.77 |
| Lactate (% DM) | 5.64 | 6.42[a] | 6.15[a] | 5.89 | 5.52 | 5.98 | 0.114 |
| Acetate (% DM) | 1.12 | 1.16 | 1.18 | 1.52[a] | 1.53[a] | 1.45[a] | 0.074 |
| Total N (% DM) | 2.20 | 2.45[a] | 2.34[a] | 2.31[a] | 2.23 | 2.35[a] | 0.022 |
| Ammonia N (% TN) | 9.62 | 9.85 | 10.1 | 10.5 | 11.54 | 10.9 | 0.544 |
| ROT (h) | 12 | 49 | 102 | 86 | 12 | 86 | 31.7 |
| CuMM-DD | 2.67 | 1.92 | 13.5 | 1.60 | 2.09 | 0.94 | 3.52 |
| In situ DMD (% DM) | 58.17 | 60.6[a] | 60.0[a] | 60.4[a] | 60.4[a] | 61.0[a] | 0.40 |
| In situ DMD-A-fraction[2] | 41.1 | 44.3[a] | 43.8[a] | 43.9[a] | 43.6[a] | 43.2 | 0.56 |
| In situ NDFD | 50.8 | 53.1[a] | 53.7[a] | 53.3[a] | 51.3 | 51.7 | 0.68 |

[1] Four silos were prepared for each treatment.
[2] Starting weight was corrected for the A-fraction.
[3] SE—standard error.
[a] Significantly different from control at P < 0.05.

Example 6

Effects of Inoculation with an Acetyl Esterase Producing Bacillus Strain Alone, and in Combination with a *Lactobacillus plantarum* Strain LP286 on Fermentation, Aerobic Stability and Digestibility of Silage Dry Matter and Fiber Ryegrass was a first cut, harvested at the Pioneer Livestock Nutrition Center (PLNC), Sheldahl, Iowa in June 2004. Acetyl esterase producing *Bacillus pumilus* strain BP5579 (see Example 1 for specific acetyl esterase activities of these strains) was grown by the Quality Control and Microbial Production Group at Pioneer Hi-Bred in Johnston, Iowa, stabilized and lyophilized as is known in the art. Similarly, *Lactobacillus plantarum* strain LP286 (ATCC# 53187) was grown by a contact manufacturer using procedures known in the art. The ryegrass was either uninoculated (control) or inoculated with LP286 at $5 \times 10^4$ colony forming units/gram forage (cfu/g), BP5579 ($1 \times 10^6$ cfu/g) or BP5579/LP286 ($1 \times 10^6 / 5 \times 10^4$ cfu/g). The treatments were applied to forage as aqueous solutions, by syringe dispersion and thoroughly mixed in to the forage by rolling the forage on a clean plastic sheet as the treatments were applied to the forage.

For each treatment, four (4) experimental 4"×14" polyvinyl chloride (PVC) pipe silos were filled and packed at 100% packing density (approximately 230 kg DM $M^3$), using a hydraulic press. Experimental silos were fitted with rubber quick caps at each end, held tight by metal rings, and the top cap was equipped with a Bunsen valve to allow gasses to escape.

Silos were opened after forty (40) days of ensilage, emptied and the forage thoroughly mixed to give a uniform mass. Silage samples were allotted to the various analyses, namely: pH, DM, Total N, Ammonia N, Lactate and VFA and in situ rumen digestibility. Dry matter was determined by drying to a constant weight in a forced air oven at 62° C. Aerobic stability assessments were concluded on individual treatment replicates using the procedure of Honig (1986) supra. The time (h) for silage temperature to rise 1.7° C. above ambient was recorded (ROT). The integration of the area between the actual silage temperature curve and the line drawn by ambient temperature (cumulative degree days or Cumm-DD) was calculated. Cumm-DD is a measure of total amount of heating.

Micro in situ bags (5.5 cm by 5.5 cm; 40 microns + or − 15; Ankom Technology Corp., Fairport, N.Y.) were used for all ruminal incubations. In situ DMD analysis was conducted as described in Example 5. NDF concentrations of the silage before and after the 48 h ruminal incubation were also determined as described in Example 5.

Ryegrass silages were well fermented as illustrated by the terminal pH value of 4.15 for the control silages (Table 9). All inoculant treatments, including BP5579 alone reduced silage pH (P<0.05) and inoculation with BP5579 or BP5579/LP286 had little or no effect on aerobic stability of silage (ROT). Inoculation with BP5579 and BP5579/LP286 increased DMD and NDFD (P<0.05). The combination of BP5579 and LP286 increased DMD and NDFD despite the fact the LP286 alone decreased DMD and tended to decrease NDFD.

Acetyl esterase producing *Bacillus pumilus* strain BP 5579 grew and established in the silo as evidence by its ability to reduce silage pH. Furthermore, BP5579 improved DMD and NDFD of grass silage when used alone or in combination with *L. plantarum* strain LP286. These data demonstrate that acetyl esterase producing *B. pumilus* is effective at improving DMD and NDFD even when used in combination with traditional silage inoculant strains, which traditional silage inoculant strains would normally be expected to dominate the *Bacillus* species during silage fermentation.

TABLE 9

PH, AEROBIC STABILITY AND DIGESTIBILITY OF FIRST CUT PRG SILAGES INOCULATED WITH *BACILLUS* STRAIN 5579, ALONE OR IN COMBINATION WITH LP286.

| Item[1] | Control | LP286 | BP5579 | BP5579/ LP286 | SE[3] |
|---|---|---|---|---|---|
| PH | 4.15 | 4.07[a] | 4.04[a] | 4.02[a] | 0.008 |
| DM | 30.1 | 36.9[a] | 29.0[a] | 29.6 | 0.165 |
| ROT (h) | 99 | 98 | 102 | 108 | 2.70 |
| CuMM-DD | 53 | 38.1 | 13.9 | 17.7 | 14.7 |
| In situ DMD (% DM) | 61.8 | 57.7 | 63.5[a] | 63.3[a] | 0.380 |
| In situ DMD-A-fraction[2] | 45.0 | 41.4 | 48.1[a] | 47.4[a] | 0.54 |
| In situ NDFD | 46.5 | 44.9 | 50.9[a] | 50.6[a] | 0.87 |

[1]Four silos were prepared for each treatment.
[2]Starting weight was corrected for the A-fraction.
[a]significantly different from control at P < 0.05.
[3]SE - standard error.

It is understood that the examples and embodiments described herein are for illustrative purposes only and that various modifications or changes in light thereof will be suggested to persons skilled in the art and are to be included within the spirit and purview of this application and scope of the appended claims.

Having illustrated and described the principles of the embodiments of the present invention, it should be apparent to persons skilled in the art that the embodiments of the invention can be modified in arrangement and detail without departing from such principles. We claim all modifications that are within the spirit and scope of the appended claims.

All publications and published patent documents cited in this specification are incorporated herein by reference to the same extent as if each individual publication or published patent document was specifically and individually indicated to be incorporated by reference.

What is claimed is:

1. A biologically pure strain of a bacterium selected from the group consisting of *Bacillus subtilis*, strain BS62, deposited as Patent Deposit No. NRRL B-30763, *Bacillus subtilis*, strain BS116, deposited as Patent Deposit No. NRRL B-30764, *Bacillus subtilis*, strain BS5482, deposited as Patent Deposit No. NRRL B-30765, *Bacillus pumilus*, strain BP5295, deposited as Patent Deposit No. NRRL B-30766, *Bacillus pumilus*, strain BP5579, deposited as Patent Deposit No. NRRL B-30767, *Bacillus subtilis*, strain BS5752, deposited as Patent Deposit No. NRRL B-30768, and mixtures thereof, wherein the bacterium enhances the digestibility of silage when added to pre-ensiled plant material in digestibility enhancing amounts.

\* \* \* \* \*